United States Patent
Kim et al.

(10) Patent No.: US 10,739,319 B2
(45) Date of Patent: Aug. 11, 2020

(54) METHOD FOR ANALYZING RELATED SUBSTANCES OF A PHARMACEUTICAL COMPOSITION CONTAINING A POLYMERIC CARRIER

(71) Applicant: SAMYANG BIOPHARMACEUTICALS CORPORATION, Seoul (KR)

(72) Inventors: Hye Rim Kim, Daejeon (KR); Ji Yeong Kim, Hanam-si (KR); Bum Chan Min, Daejeon (KR); Min Hyo Seo, Daejeon (KR); Ho Joon Choi, Uiwang-si (KR)

(73) Assignee: SAMYANG BIOPHARMACEUTICALS CORPORATION, Seoul (KR)

(*) Notice: Subject to any disclaimer, the term of this patent is extended or adjusted under 35 U.S.C. 154(b) by 112 days.

(21) Appl. No.: 15/747,845

(22) PCT Filed: Jul. 28, 2016

(86) PCT No.: PCT/KR2016/008262
§ 371 (c)(1),
(2) Date: Jan. 26, 2018

(87) PCT Pub. No.: WO2017/018814
PCT Pub. Date: Feb. 2, 2017

(65) Prior Publication Data
US 2018/0224405 A1  Aug. 9, 2018

(30) Foreign Application Priority Data
Jul. 28, 2015 (KR) .................. 10-2015-0106624

(51) Int. Cl.
*G01N 33/15* (2006.01)
*A61K 31/337* (2006.01)
(Continued)

(52) U.S. Cl.
CPC ............ *G01N 30/36* (2013.01); *A61K 9/107* (2013.01); *A61K 31/337* (2013.01); *G01N 30/52* (2013.01);
(Continued)

(58) Field of Classification Search
CPC ................... G01N 2030/8872; A61K 31/337
See application file for complete search history.

(56) References Cited

U.S. PATENT DOCUMENTS 6,322,805 B1   11/2001  Kim et al.
2003/0157170 A1*  8/2003  Liggins .................. A61P 35/00
                                                           424/468

(Continued)

FOREIGN PATENT DOCUMENTS

EP    2522338 A2     11/2012
JP    2012-513984 A   6/2012

(Continued)

OTHER PUBLICATIONS

Volk, K.J. et al. "Profiling degradants of paclitaxel using liquid chromatography—mass spectrometry and liquid chromatography—tandem mass spectrometry substructural techniques," Journal of Chromatography B, 696 (1997) 99-115 (Year: 1997).*

(Continued)

*Primary Examiner* — Christopher Adam Hixson
*Assistant Examiner* — Michelle Adams
(74) *Attorney, Agent, or Firm* — Birch, Stewart, Kolasch & Birch, LLP

(57) ABSTRACT

A method for analyzing related substances in a pharmaceutical composition containing an amphiphilic block copolymer comprising a hydrophilic block and a hydrophobic block as a polymeric drug carrier, related substances identified thereby, and a method for evaluating a pharmaceutical composition by using the same are provided. Preferably, the
(Continued)

method comprises evaluating a polymeric micelle pharmaceutical composition, which comprises an amphiphilic block copolymer comprising a hydrophilic block (A) and a hydrophobic block (B), and paclitaxel or docetaxel as a poorly water-soluble drug, by using a compound represented by Chemical Formula 1, wherein the hydrophilic block (A) comprises one or more selected from the group consisting of polyethylene glycol or derivatives thereof, polyvinylpyrrolidone, polyvinyl alcohol, polyacrylamide and combinations thereof; and the hydrophobic block (B) is polylactide.

13 Claims, 11 Drawing Sheets

(51) Int. Cl.

| | | |
|---|---|---|
| *G01N 30/36* | (2006.01) | |
| *G01N 30/72* | (2006.01) | |
| *G01N 30/88* | (2006.01) | |
| *A61K 9/107* | (2006.01) | |
| *G01N 30/52* | (2006.01) | |
| *G01N 24/08* | (2006.01) | |
| *C07D 305/14* | (2006.01) | |

(52) U.S. Cl.
CPC ......... *G01N 30/7233* (2013.01); *G01N 30/88* (2013.01); *G01N 33/15* (2013.01); *C07D 305/14* (2013.01); *G01N 24/08* (2013.01); *G01N 2030/525* (2013.01); *G01N 2030/885* (2013.01); *G01N 2030/8872* (2013.01)

(56) References Cited

U.S. PATENT DOCUMENTS

| | | |
|---|---|---|
| 2004/0151690 A1 | 8/2004 | Nakanishi et al. |
| 2011/0076308 A1 | 3/2011 | Kwon |
| 2011/0251269 A1 | 10/2011 | Seo et al. |
| 2014/0099263 A1 | 4/2014 | Eliasof et al. |
| 2017/0028068 A1* | 2/2017 | Kim ................. A61K 47/32 |

FOREIGN PATENT DOCUMENTS

| | | |
|---|---|---|
| JP | 2013-516407 A | 5/2013 |
| JP | 2013-541022 A | 11/2013 |
| KR | 10-2004-0030693 A | 4/2004 |
| KR | 10-2010-0076862 A | 7/2010 |
| WO | WO 2009/084801 A1 | 7/2009 |
| WO | WO 2010/074379 A1 | 7/2010 |
| WO | WO 2012/058619 A1 | 5/2012 |

OTHER PUBLICATIONS

Pyo, S.-H. et al. "Evaluation of paclitaxel rearrangement involving opening of theoxetane ring and migration of acetyl and benzoyl groups," Journal of Pharmaceutical and Biomedical Analysis 43 (2007) 1141-1145 (Year: 2007).*

Richheimer, S.L. et al. "High-Performance Liquid Chromatographic Assay of Taxol," Anal. Chem. 1992, 64, 2323-2326 (Year: 1992).*

Ciutaru et al., "A HPLC validated assay of paclitaxel's related impurities in pharmaceutical forms containing Cremophor® EL", Elsevier, Journal of Pharmaceutical and Biomedical Analysis, vol. 34, 2004, pp. 493-499.

International Search Report (PCT/ISA/210) issued in PCT/KR2016/008262, dated Nov. 1, 2016.

Kumar et al., "Isolation and characterization of degradation impurities in docetaxel drug substance and its formulation", Elsevier, Journal of Pharmaceutical and Biomedical Analysis, vol. 43, 2007, pp. 1228-1235.

Written Opinion (PCT/ISA/237) issued in PCT/KR2016/008262, dated Nov. 1, 2016.

Xia et al., "Validated HPLC Method for the Determination of Paclitaxel-related Substances in an Intravenous Emulsion Loaded with a Paclitaxel-Cholesterol Complex", Indian Journal of Pharmaceutical Sciences, vol. 75, No. 6, Nov.-Dec. 2013, pp. 672-679.

European Search Report for Appl. No. 16830847.6 dated May 24, 2019.

* cited by examiner

[Fig. 1]
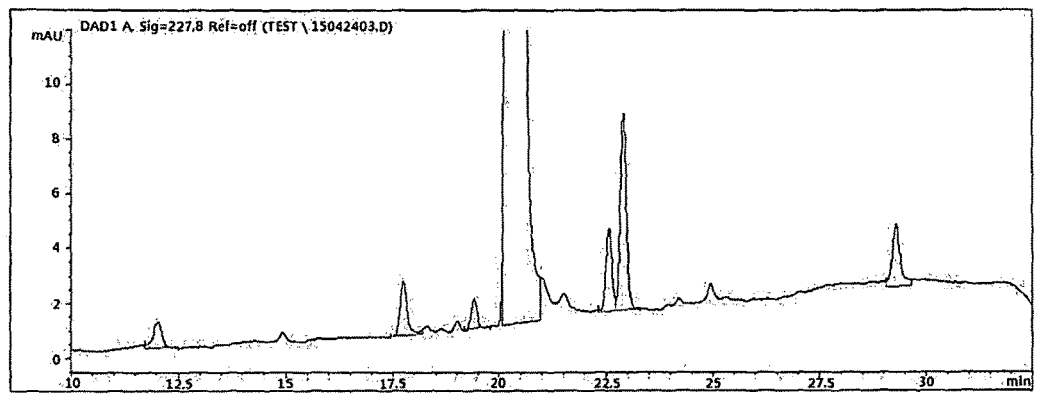
[Fig. 2]
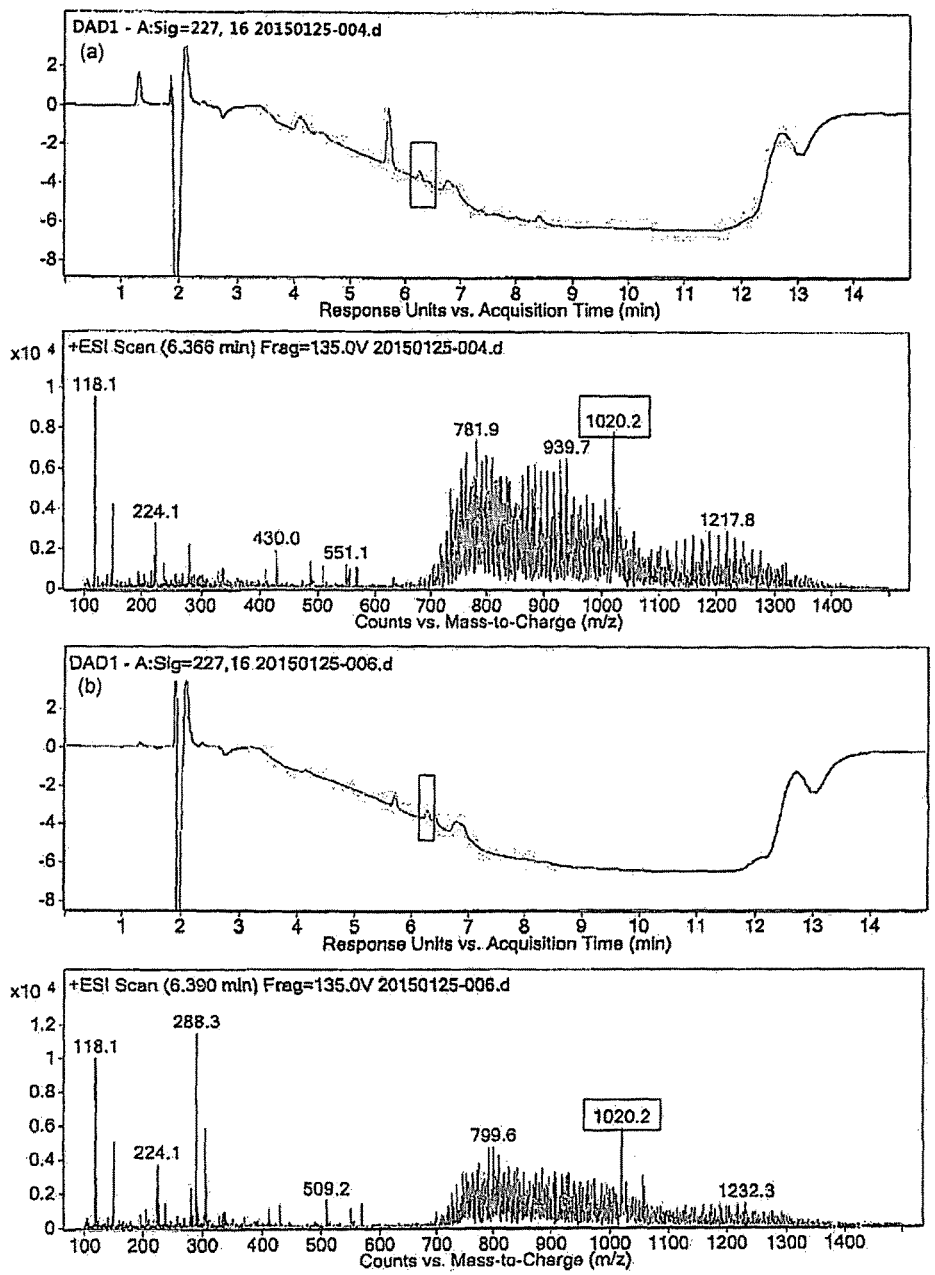

[Fig. 3]
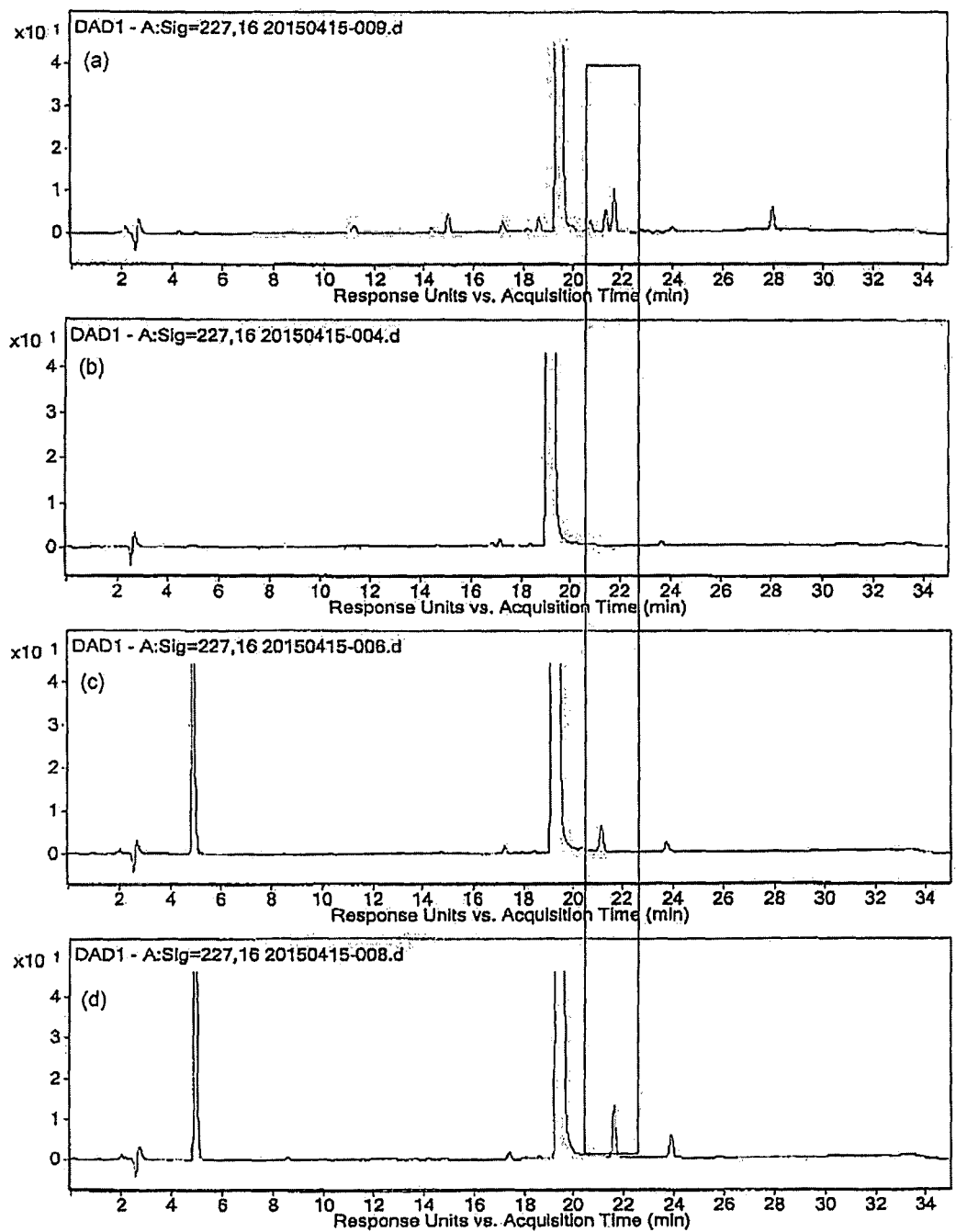

[Figure 5]
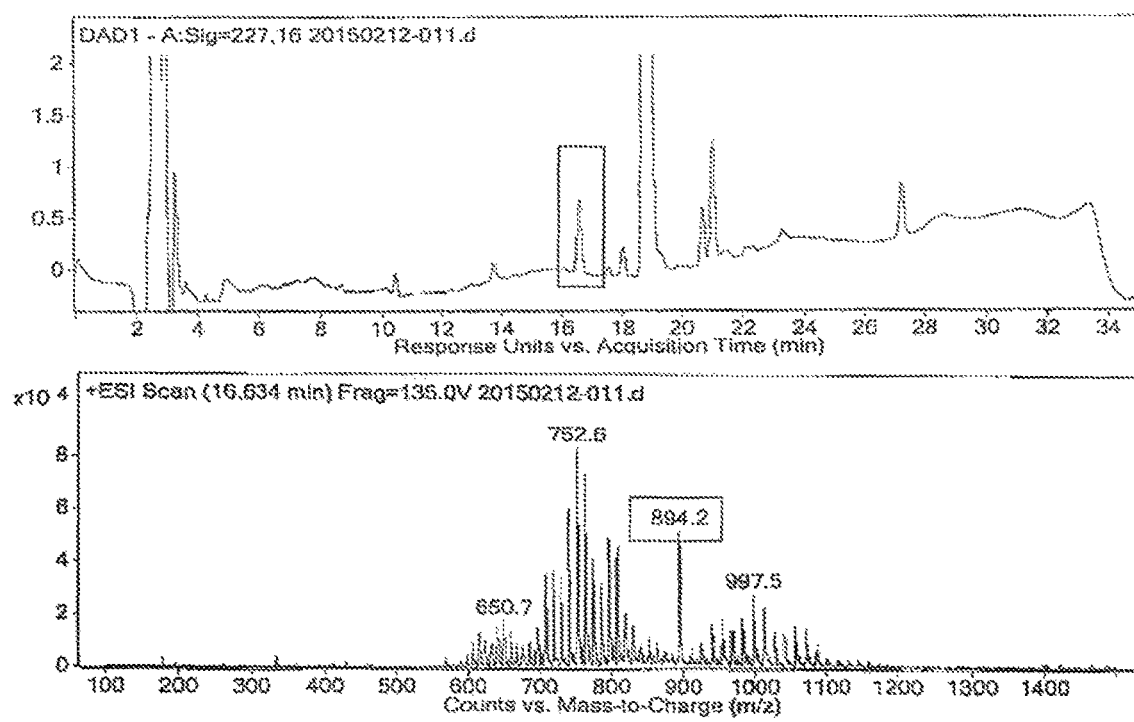

[Fig. 6]
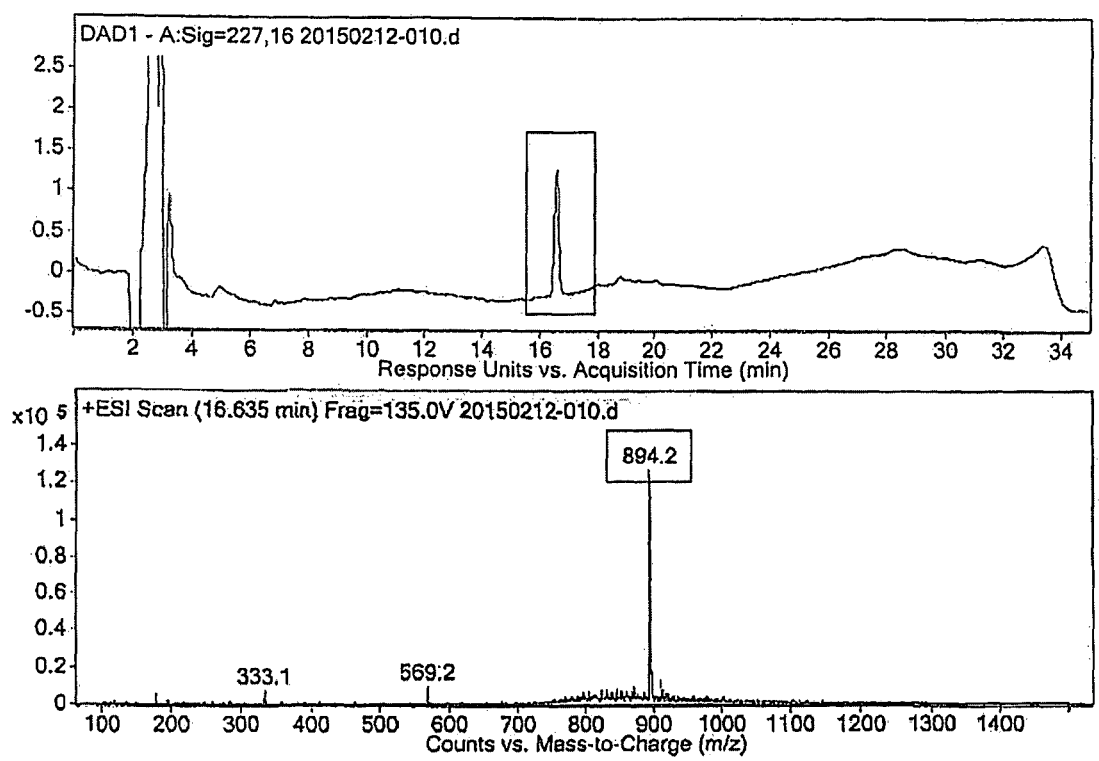

[Fig. 7]
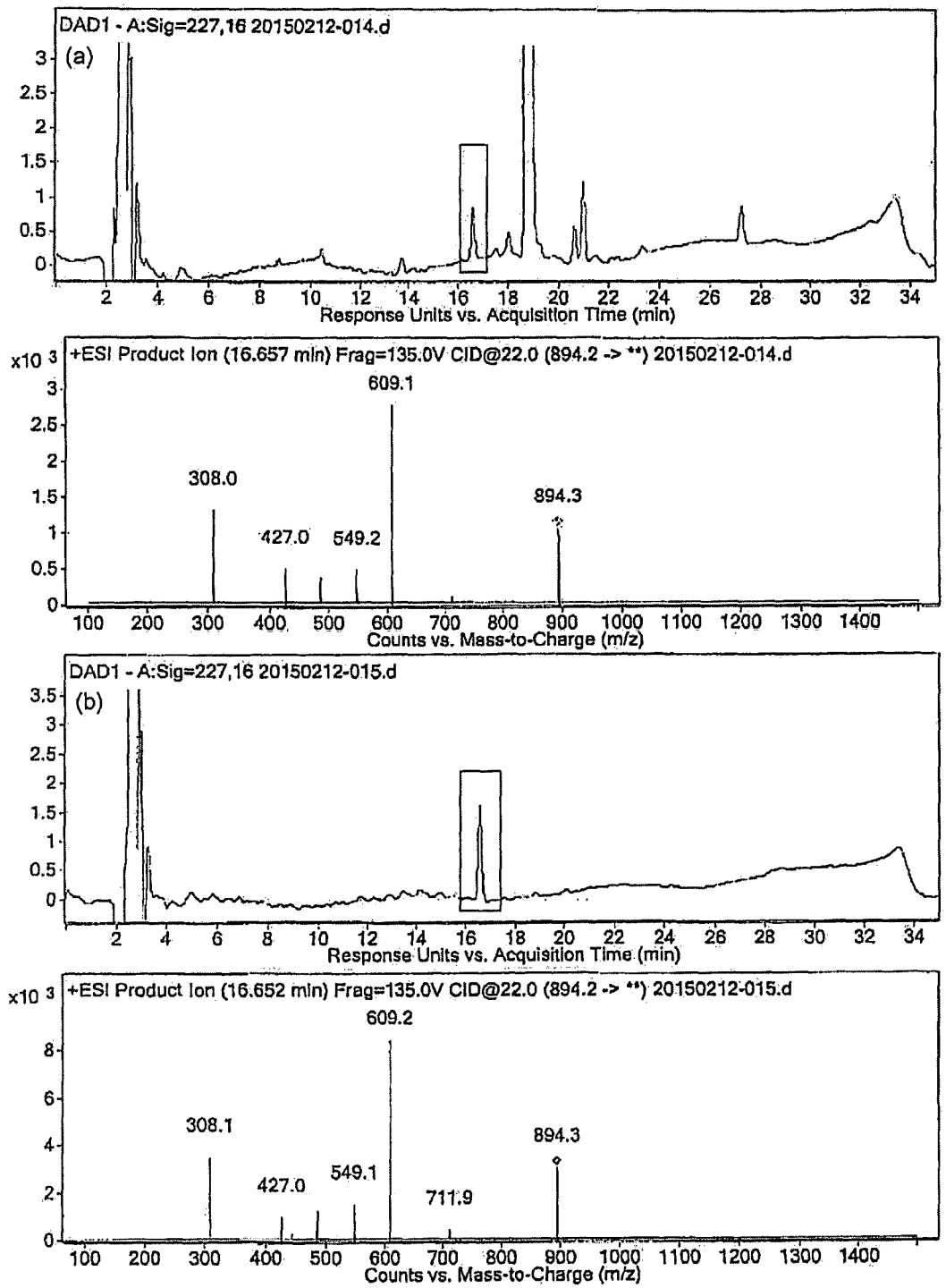

[Fig. 8]
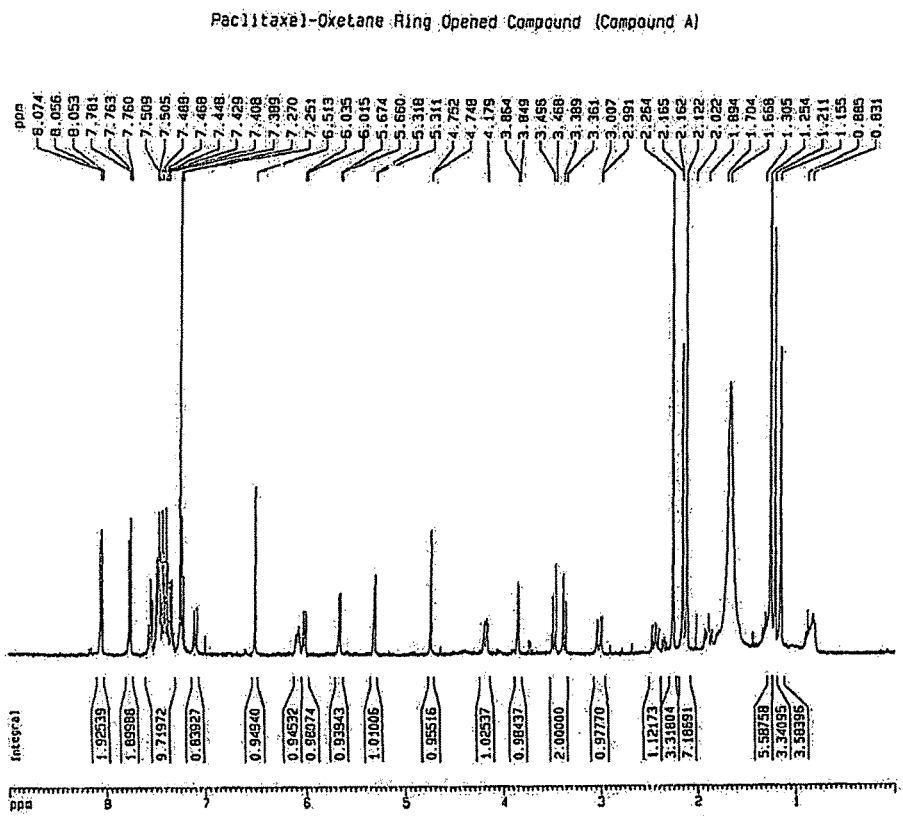
[Fig. 9]
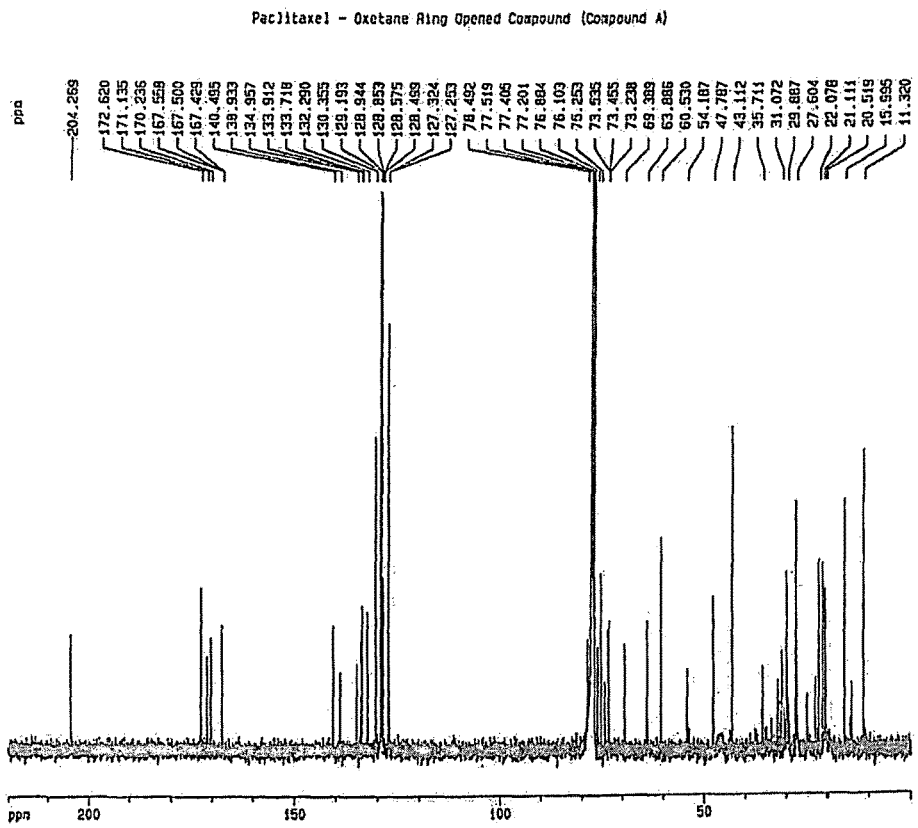

[Fig. 10]
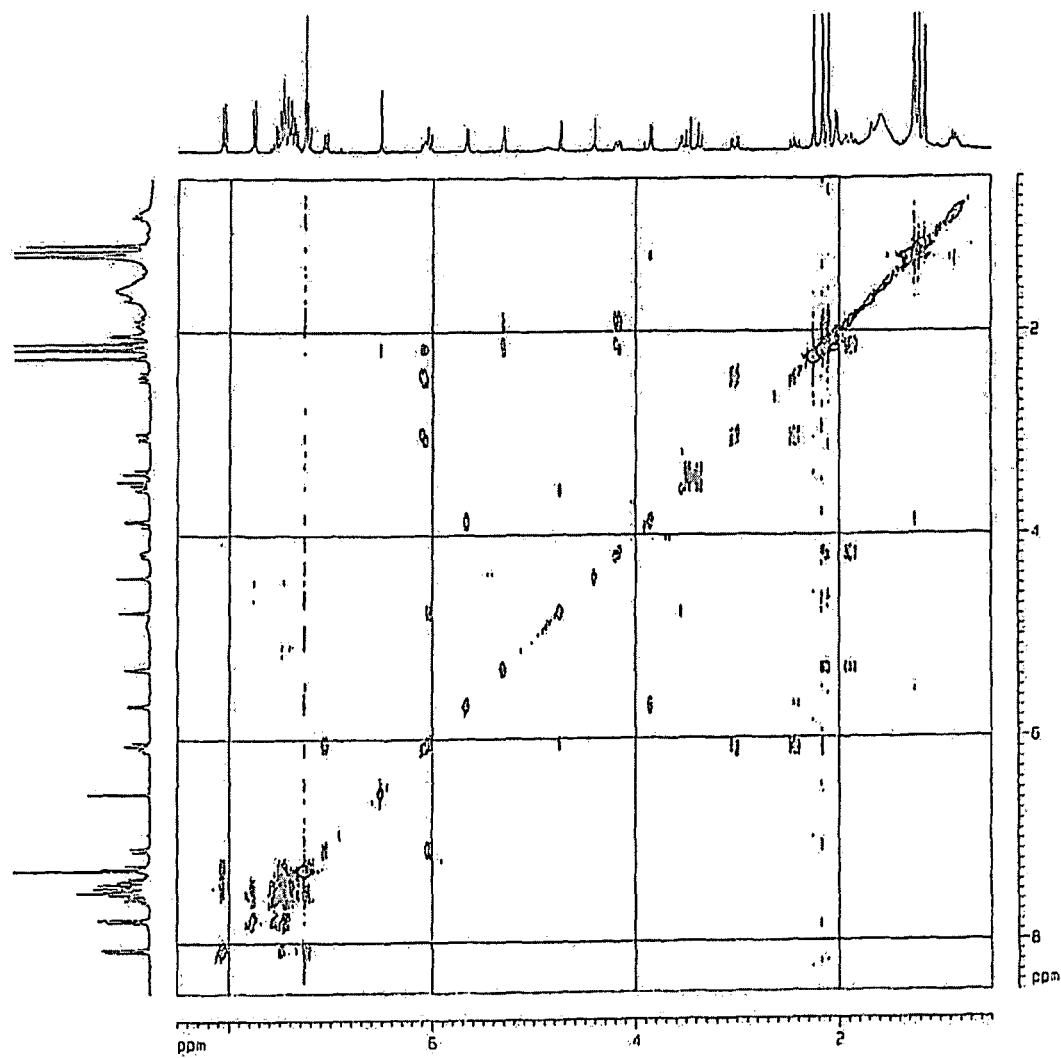

[Fig. 11]
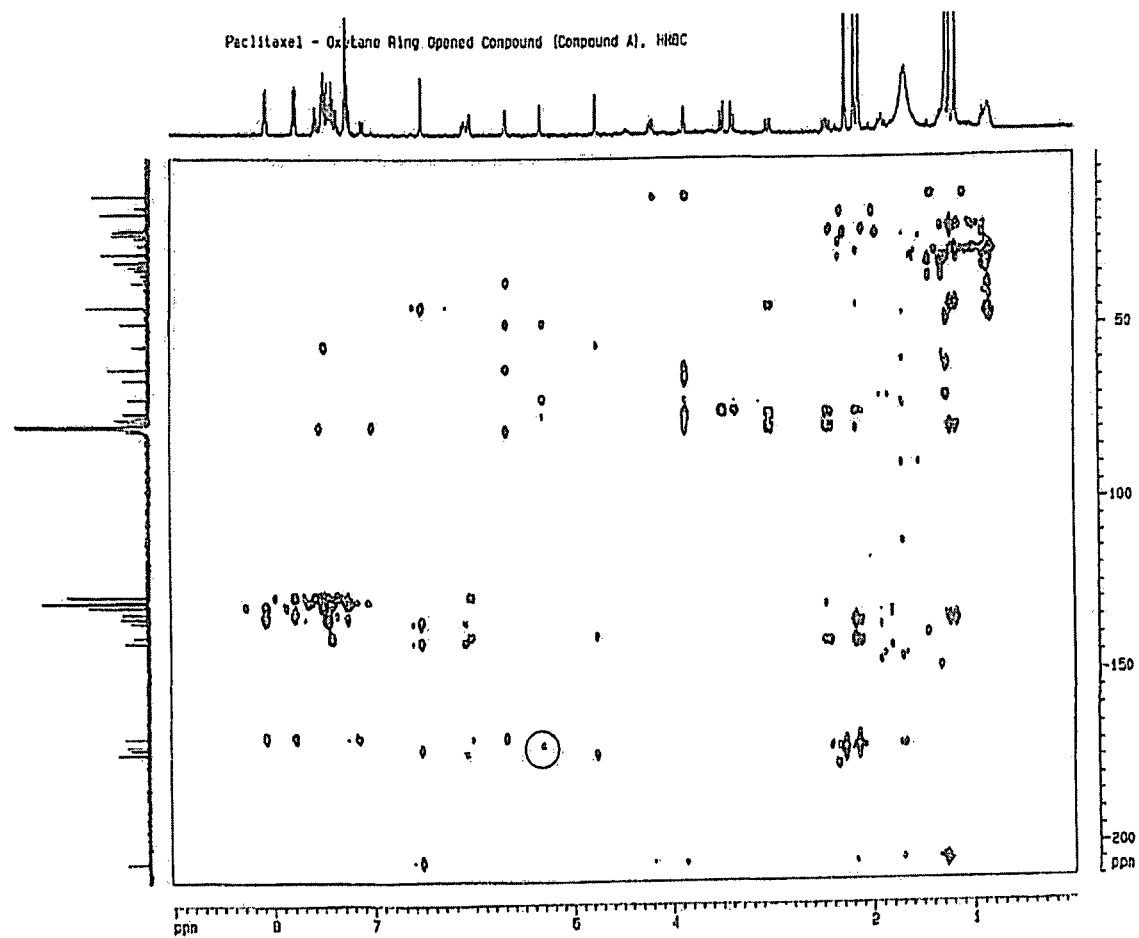

METHOD FOR ANALYZING RELATED SUBSTANCES OF A PHARMACEUTICAL COMPOSITION CONTAINING A POLYMERIC CARRIER

TECHNICAL FIELD

The present disclosure relates to a method for analyzing related substances of a pharmaceutical composition containing a polymeric drug carrier, and more specifically, a method for analyzing related substances in a pharmaceutical composition containing an amphiphilic block copolymer comprising a hydrophilic block and a hydrophobic block as a polymeric drug carrier, related substances identified thereby, and a method for evaluating a pharmaceutical composition by using the same. According to an embodiment of the present invention, it is possible to analyze impurities generated in final drug products, etc. precisely and accurately.

BACKGROUND ART

Solubilization of a poorly water-soluble drug is a key technology for delivering the drug into the body via oral or parenteral administration. Such solubilization methods include a method of adding a surfactant to an aqueous solution to form micelles and then entrapping a poorly water-soluble drug therein.

An amphiphilic block copolymer used as a surfactant comprises a hydrophilic polymer block and a hydrophobic polymer block. Since the hydrophilic polymer block directly contacts blood proteins and cell membranes in vivo, polyethylene glycol or monomethoxypolyethylene glycol, etc. having biocompatibility has been used. The hydrophobic polymer block improves affinity to a hydrophobic drug, and polylactide, polyglycolide, poly(lactic-glycolide), polycaprolactone, polyamino acid or polyorthoester, etc. having biodegradability has been used. In particular, polylactide derivatives have been applied to drug carriers in various forms because they have excellent biocompatibility and are hydrolyzed into harmless lactic acid in vivo. Polylactide derivatives have various physical properties depending on their molecular weights, and have been developed in various forms such as microsphere, nanoparticle, polymeric gel and implant agent.

U.S. Pat. No. 6,322,805 discloses a composition for delivering a poorly water-soluble drug consisting of a polymeric micelle-type drug carrier and a poorly water-soluble drug, wherein the polymeric micelle-type drug carrier is formed from a diblock or triblock copolymer which is not crosslinked by a crosslinking agent and consists of at least one biodegradable hydrophobic polymer selected from the group consisting of polylactide, polyglycolide, poly(lactide-glycolide), polycaprolactone and derivatives thereof and poly(alkylene oxide) as a hydrophilic polymer, wherein the poorly water-soluble drug is physically entrapped in the drug carrier and solubilized, and wherein the polymeric micelle-type drug carrier forms a clear aqueous solution in water and effectively delivers the poorly water-soluble drug into the body.

However, the above pharmaceutical composition comes to have an increased amount of related substances with the lapse of storage time. To analyze the related substances in the composition, an analysis method of using C18 column has been used, but it does not have a sufficient resolution to isolate some related substances. In particular, since the resolution of 10-deacetyl-7-epipaclitaxel (impurity B)—which is one of the representative related substances of paclitaxel—and paclitaxel is 0.95 or lower, they are not completely isolated and there has been a need to improve the resolution. In addition, the two unknown impurities shown at relative retention time (RRT) 1.14 as the related substances observed during the long-term storage test for six months or longer or the severe condition test are detected as one peak, not being isolated from each other. Furthermore, in order to analyze a very small amount of related substance with a similar method, the injection amount of the sample must be increased largely as compared with one for content test.

Accordingly, there has been a need to develop an analysis method which can isolate the impurities in the course of production and marketing of the pharmaceutical composition, and has a sufficient sensitivity so that a very small amount of each related substance can be accurately quantified without increasing the injection amount of the sample.

CONTENTS OF THE INVENTION

Problems to be Solved

One purpose of the present invention is to provide a method for analyzing related substances of a pharmaceutical composition containing a polymeric drug carrier, which has improved resolution and sensitivity, and is easy to use.

Another purpose of the present invention is to provide a related substance analyzed and identified by the above method.

Yet another purpose of the present invention is to provide a method for evaluating a pharmaceutical composition containing a polymeric drug carrier by using the above related substance as a standard material.

Technical Means to Solve the Problems

One aspect of the present invention provides a method for analyzing related substances of a polymeric micelle pharmaceutical composition, comprising: (1) preparing a sample for analysis of a polymeric micelle pharmaceutical composition comprising an amphiphilic block copolymer comprising a hydrophilic block (A) and a hydrophobic block (B), and a poorly water-soluble drug; and (2) analyzing the prepared sample by High Performance Liquid Chromatography (HPLC) under the following conditions (a) and (b):

(a) a stationary phase of porous particles having a particle size of 4 μm or less; and (b) a column having an inner diameter of 5 mm or less and a length of 50 mm or more.

Another aspect of the present invention provides a compound represented by the following Formula 1c:

[Formula 1c]

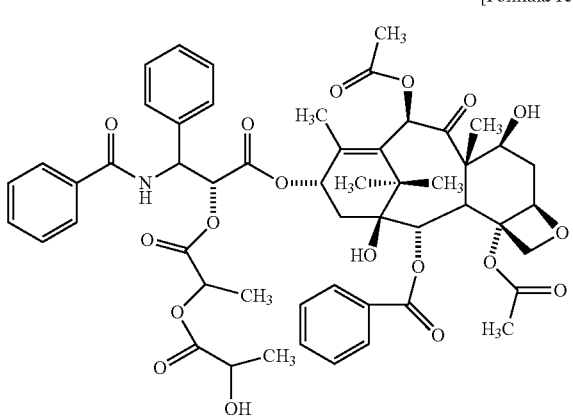

Yet another aspect of the present invention provides a method for evaluating a polymeric micelle pharmaceutical composition comprising evaluating a polymeric micelle pharmaceutical composition, which comprises an amphiphilic block copolymer comprising a hydrophilic block (A) and a hydrophobic block (B), and paclitaxel or docetaxel as a poorly water-soluble drug, by using a compound represented by the following Formula 1 or a compound represented by the following Formula 2 as a standard material:

[Formula 1]

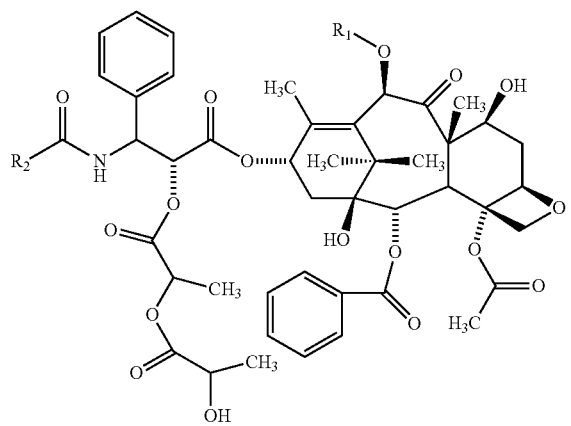

[Formula 2]

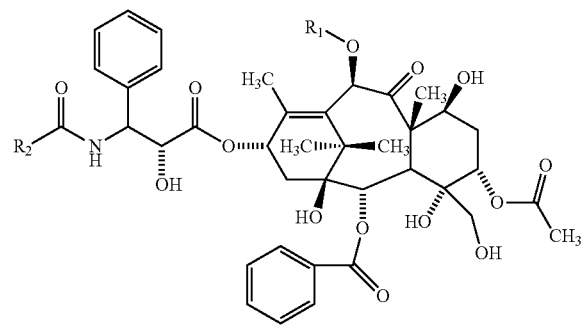

wherein
$R_1$ is H or $COCH_3$, and $R_2$ is phenyl or $OC(CH_3)_3$.

Effects of the Invention

According to an embodiment of the present invention, impurities generated in final drug products, etc. can be analyzed precisely by using related substances of a pharmaceutical composition containing a polymeric carrier and a poorly water-soluble drug, as a standard material. In addition, generation of related substances can be prevented basically, thereby to reduce an amount of related substances finally.

BRIEF EXPLANATION OF THE DRAWINGS

FIG. 1 is the resulting chromatogram of HPLC analysis for the polymeric micelle composition containing paclitaxel used in Experimental Example 1-1, which had been subjected to six-month acceleration test.

FIG. 2 is the resulting chromatogram and spectrum of LC/MS/MS analysis conducted in Experimental Example 1-2 for the related substances isolated in Experimental Example 1-1:
(a) RRT 1.10±0.02 (1.08~1.12) (hereinafter, RRT 1.10 is interchangeably used with RRT 1.10±0.02)
(b) RRT 1.12±0.02 (1.10~1.14) (hereinafter, RRT 1.12 is interchangeably used with RRT 1.12±0.02)

FIG. 3 is the resulting chromatogram of HPLC analysis for the induced reaction product obtained in Experimental Example 2:
(a) Polymeric micelle pharmaceutical composition containing paclitaxel
(b) Paclitaxel
(c) Reaction product of paclitaxel and L-lactide
(d) Reaction product of paclitaxel and D-lactide
FIG. 4A: Paclitaxel
FIG. 4B: Reaction product of paclitaxel and L-lactide
FIG. 4C: Reaction product of paclitaxel and D-lactide
FIG. 5 shows the results of LC/MS/MS analysis for the related substance obtained at RRT 0.87±0.02 position (hereinafter, RRT 0.87 is interchangeably used with RRT 0.87±0.02) in Experimental Example 1-1.

FIG. 6 shows the results of LC/MS/MS analysis for the material obtained at RRT 0.87 by treating paclitaxel with acid and using the same analysis method as in Experimental Example 5.

FIG. 7 shows the results of product ion scan in the LC/MS/MS analysis for the material obtained at RRT 0.87 by treating paclitaxel with acid and using the same analysis method as in Experimental Example 5, together with the analysis results of the related substance at RRT 0.87 position in the polymeric micelle pharmaceutical composition containing paclitaxel:
(a) Results of analysis of the polymeric micelle pharmaceutical composition containing paclitaxel after the six-month acceleration test
(b) Results of analysis of the material obtained at RRT 0.87 by treating paclitaxel with acid and using the same analysis method FIG. 8 shows the results of $^1$H NMR analysis in the NMR analysis for the material obtained at RRT 0.87 by treating paclitaxel with acid and using the same analysis method as in Experimental Example 5.

FIG. 9 shows the results of $^{13}$C NMR analysis in the NMR analysis for the material obtained at RRT 0.87 by treating paclitaxel with acid and using the same analysis method as in Experimental Example 5.

FIG. 10 shows the results of COSY (Correlation Spectroscopy) analysis in the NMR analysis for the material obtained at RRT 0.87 by treating paclitaxel with acid and using the same analysis method as in Experimental Example 5.

FIG. 11 shows the results of HMBC (Heteronuclear Multiple Bond Correlation Spectroscopy) analysis in the NMR analysis for the material obtained at RRT 0.87 by treating paclitaxel with acid and using the same analysis method as in Experimental Example 5.

DETAILED DESCRIPTION TO CARRY OUT THE INVENTION

Figure 4A:
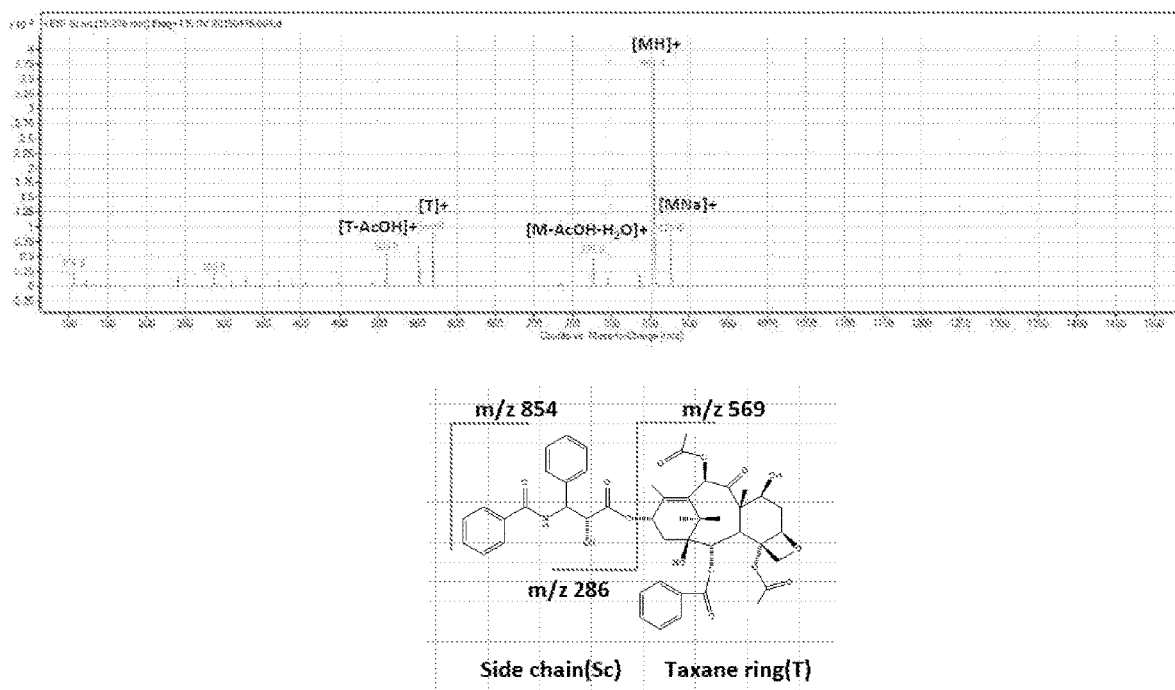
FIG. 4A, FIG. 4b and FIG. 4C are the resulting chromatogram of LC/MS/MS analysis for the induced reaction product obtained in Experimental Example 3.

The present invention is explained in more detail below.

As used herein, the term "related substance" is referred to as a kind of impurity to the main active ingredient, which can be contained during the process of raw material synthesis or in the final drug product and used for quality evaluation, etc. of the final drug product.

The method for analyzing related substances of a polymeric micelle pharmaceutical composition according to an embodiment of the present invention comprises: (1) preparing a sample for analysis of a polymeric micelle pharmaceutical composition comprising an amphiphilic block copolymer comprising a hydrophilic block (A) and a hydrophobic block (B), and a poorly water-soluble drug; and (2) analyzing the prepared sample by High Performance Liquid Chromatography (HPLC) under the following conditions (a) and (b):

(a) a stationary phase of porous particles having a particle size of 4 μm or less; and (b) a column having an inner diameter of 5 mm or less and a length of 50 mm or more.

According to one embodiment of the present invention, the stationary phase of porous particles can be a pentafluorophenyl stationary phase.

In an embodiment of the present invention, it is possible to use High Performance Liquid Chromatography (HPLC) using (a) a stationary phase of porous particles having a particle size of 1.5 to 4 μm; and (b) a column having an inner diameter of 2 to 5 mm and a length of 50 to 250 mm.

According to one embodiment of the present invention, the method for analyzing related substances of the present invention can further comprise (3) qualitatively analyzing the related substances isolated in the above step (2) by LC/MS (Liquid Chromatography/Mass Spectrometry), LC/MS/MS (Liquid Chromatography/Tandem Mass Spectrometry), NMR or a combination thereof.

In the above further step of qualitative analysis, LC/MS or LC/MS/MS can be one using (c) a hybrid ODS (octadecyl-silica) stationary phase and (d) a column having an inner diameter of 10 mm or less and a length of 500 mm or less. According to an example, a column having an inner diameter of 1 to 10 mm and a length of 10 to 150 mm can be used.

According to one embodiment of the present invention, the method for analyzing related substances can use a UV detector to detect the related substances.

The pharmaceutical composition used in an embodiment of the present invention comprises, as essential components, a polymeric carrier which is an amphiphilic block copolymer comprising a hydrophilic block (A) and a hydrophobic block (B), and a poorly water-soluble drug which is entrapped within the carrier.

According to one embodiment of the present invention, the amphiphilic block copolymer comprises an A-B type diblock copolymer consisting of a hydrophilic block (A) and a hydrophobic block (B), or a B-A-B type triblock copolymer.

According to one embodiment of the present invention, the amphiphilic block copolymer may comprise the hydrophilic block in an amount of 20 to 95% by weight, and more concretely 40 to 95% by weight, based on the total weight of the copolymer. In addition, the amphiphilic block copolymer may comprise the hydrophobic block in an amount of 5 to 80% by weight, and more concretely 5 to 60% by weight, based on the total weight of the copolymer.

According to one embodiment of the present invention, the amphiphilic block copolymer may have a number average molecular weight of 1,000 to 50,000 Daltons, and more concretely 1,500 to 20,000 Daltons.

According to one embodiment of the present invention, the hydrophilic block is a polymer having biocompatibility and may comprise one or more selected from the group consisting of polyethylene glycol or derivatives thereof, polyvinylpyrrolidone, polyvinyl alcohol, polyacrylamide and combinations thereof, and more concretely, it may comprise one or more selected from the group consisting of polyethylene glycol, monomethoxypolyethylene glycol and combinations thereof. The hydrophilic block may have a number average molecular weight of 200 to 20,000 Daltons, and more concretely 200 to 10,000 Daltons.

According to one embodiment of the present invention, the hydrophobic block is a polymer having biodegradability and may be a polymer of monomers derived from alpha (α)-hydroxy acid. Concretely, it may comprise one or more selected from the group consisting of polylactide, polyglycolide, polymandelic acid, polycaprolactone, polydioxan-2-one, polyamino acid, polyorthoester, polyanhydride, polycarbonate and combinations thereof, and more concretely, it may comprise one or more selected from the group consisting of polylactide, polyglycolide, polycaprolactone, polydioxan-2-one and combinations thereof. The hydrophobic block may have a number average molecular weight of 200 to 20,000 Daltons, and more concretely 200 to 10,000 Daltons.

According to one embodiment of the present invention, an amphiphilic block copolymer comprising a hydrophobic polymer block of poly(alpha (α)-hydroxy acid) may be synthesized by a known ring-opening polymerization method using a hydrophilic polymer having hydroxyl group as an initiator, and a lactone monomer of alpha (α)-hydroxy acid. For example, L-lactide or D,L-lactide may be polymerized with hydrophilic polyethylene glycol or monomethoxypolyethylene glycol having hydroxyl group as an initiator by ring-opening. Synthesis of diblock or triblock copolymer is possible according to the number of hydroxyl group existing in the hydrophilic block which is the initiator. In the ring-opening polymerization, an organometallic catalyst such as tin oxide, lead oxide, tin octoate, antimony octoate, etc. may be used, and tin octoate having biocompatibility is preferably used in preparing polymer for medical use.

In an embodiment of the present invention, the poorly water-soluble drug entrapped within the polymeric carrier can be an anticancer agent, more concretely a taxane anticancer agent. In an embodiment of the present invention, taxane may be an anhydrous form or a hydrated form, and an amorphous form or a crystalline form. In addition, the taxane may be extracted from natural plants, or obtained through semi-synthesis or plant cell culture method, etc.

The taxane anticancer agent can be one or more selected from the group consisting of paclitaxel, docetaxel, 7-epipaclitaxel, t-acetylpaclitaxel, 10-desacetylpaclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel and cabazitaxel, and more concretely, it can be paclitaxel, docetaxel or a combination thereof.

The pharmaceutical composition of an embodiment of the present invention may comprise the poorly water-soluble drug in an amount of 0.1 to 50 parts by weight, and more concretely 0.5 to 30 parts by weight, based on 100 parts by weight of the amphiphilic block copolymer. If the amount of the poorly water-soluble drug is too small as compared with that of the amphiphilic block copolymer, the weight ratio of the amphiphilic copolymer used per drug is high and thus the time for reconstitution may increase. On the other hand, if the amount of the poorly water-soluble drug is too large, there may be a problem of rapid precipitation of the poorly water-soluble drug.

According to one embodiment of the present invention, the related substance detected in the method for analyzing related substance of the present invention may include a compound represented by the following Formula 1:

[Formula 1]

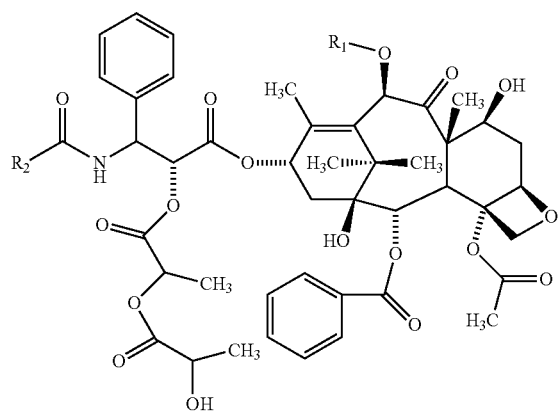

wherein
$R_1$ is H or $COCH_3$, and $R_2$ is phenyl or $OC(CH_3)_3$.

The compound of the above Formula 1 may include a compound of the following Formula 1a, a compound of the following Formula 1b, or both of them:

[Formula 1a]

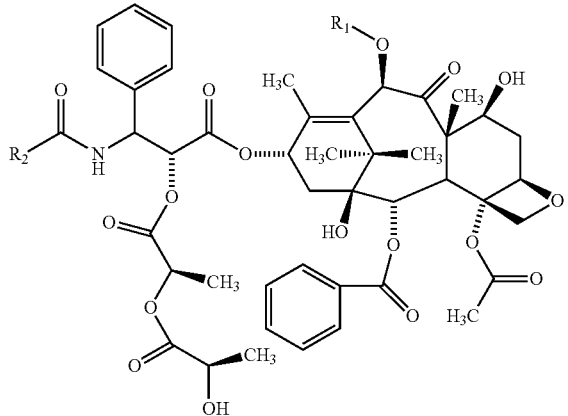

[Formula 1b]

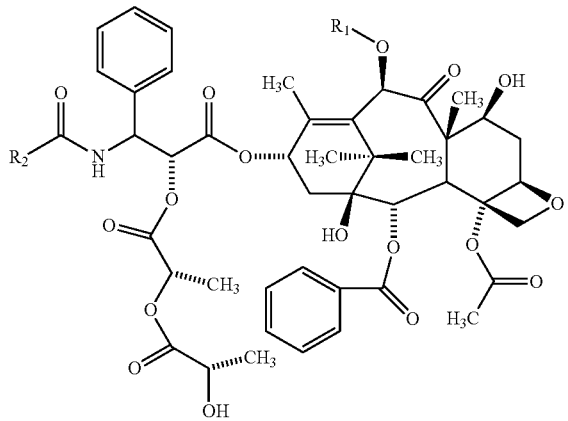

According to one embodiment of the present invention, the poorly water-soluble drug is paclitaxel, and the related substance may include the compound represented by the following Formula 1c:

[Formula 1c]

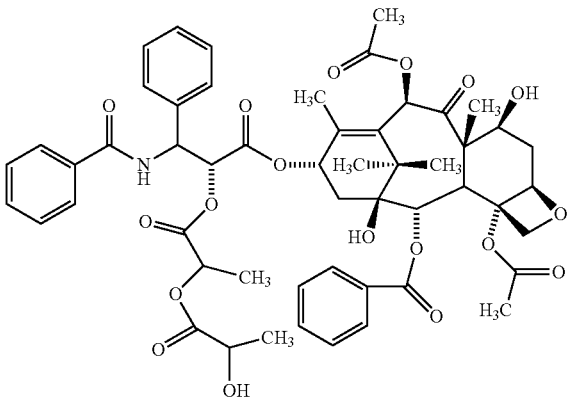

The compound of Formula 1c may include the compound of the following Formula 1d, the compound of the following Formula 1e, or both of them:

[Formula 1d]

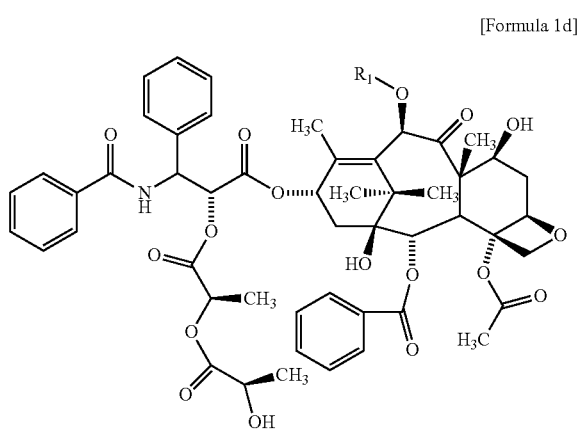

[Formula 1e]

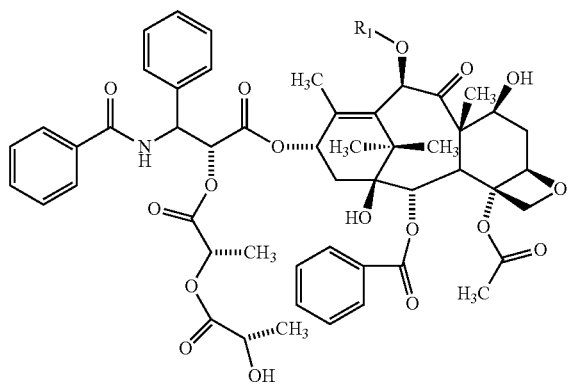

According to one embodiment of the present invention, the related substance detected in an embodiment of the present invention may include a compound represented by the following Formula 2:

[Formula 2]

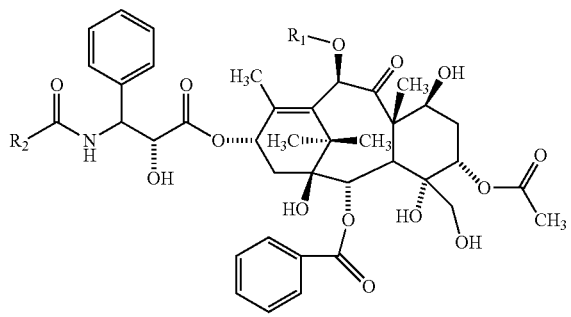

wherein

R$_1$ is H or COCH$_3$, and R$_2$ is phenyl or OC(CH$_3$)$_3$.

According to one embodiment of the present invention, the poorly water-soluble drug is paclitaxel, and the related substance may include the compound represented by the following Formula 2a:

[Formula 2a]

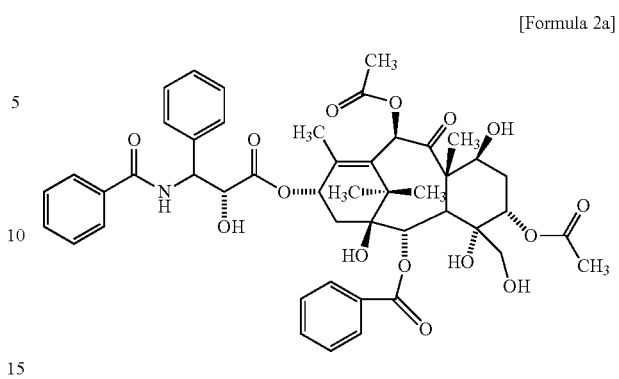

As another aspect of the present invention, a method for evaluating a polymeric micelle pharmaceutical composition comprises evaluating a polymeric micelle pharmaceutical composition. which comprises an amphiphilic block copolymer comprising a hydrophilic block (A) and a hydrophobic block (B), and paclitaxel or docetaxel as a poorly water-soluble drug, by using a compound represented by the above Formula 1 or a compound represented by the above Formula 2 as a standard material.

The compound of the above Formula 1 may include a compound of Formula 1a, a compound of Formula 1b, or both of them.

According to one embodiment of the present invention, in the above method for evaluating a polymeric micelle pharmaceutical composition, the poorly water-soluble drug is paclitaxel, and the standard material may be a compound represented by the above Formula 1c or Formula 2a.

The compound of the above Formula 1c may include a compound of Formula 1 d, a compound of Formula 1e, or both of them.

As used herein, the "initial" amount of the poorly water-soluble drug means the weight of the poorly water-soluble drug incorporated when the pharmaceutical composition was prepared.

In the method for evaluating a polymeric micelle pharmaceutical composition of an embodiment of the present invention, it can be recognized that the quality standard is satisfied if the pharmaceutical composition contains, when stored at the accelerated condition (40° C.) for 6 months, a related substance of Formula 1 (particularly, Formula 1c) in an amount of 0.8 part by weight or less, preferably 0.65 part by weight or less, more preferably 0.5 part by weight or less, even more preferably 0.35 part by weight or less, and most preferably 0.2 part by weight or less, based on 100 parts by weight of the initial amount of the poorly water-soluble drug.

In the method for evaluating a polymeric micelle pharmaceutical composition of an embodiment of the present invention, it can be recognized that the quality standard is satisfied if the pharmaceutical composition contains, when stored at the accelerated condition (40° C.) for 6 months, a related substance of Formula 1a (particularly, Formula 1d) in an amount of 0.3 part by weight or less, preferably 0.25 part by weight or less, more preferably 0.2 part by weight or less, even more preferably 0.15 part by weight or less, and most preferably 0.1 part by weight or less, based on 100 parts by weight of the initial amount of the poorly water-soluble drug.

In the method for evaluating a polymeric micelle pharmaceutical composition of an embodiment of the present invention, it can be recognized that the quality standard is satisfied if the pharmaceutical composition contains, when stored at the accelerated condition (40° C.) for 6 months, a related substance of Formula 1b (particularly, Formula 1e) in an amount of 0.5 part by weight or less, preferably 0.4 part by weight or less, more preferably 0.3 part by weight or less, even more preferably 0.2 part by weight or less, and most preferably 0.1 part by weight or less, based on 100 parts by weight of the initial amount of the poorly water-soluble drug.

In a preferable embodiment of the method for evaluating a polymeric micelle pharmaceutical composition of an embodiment of the present invention, it can be recognized that the quality standard is satisfied if the pharmaceutical composition contains, when stored at the accelerated condition (40° C.) for 6 months, a related substance of Formula 1 (particularly, Formula 1c) in an amount of less than 0.8 part by weight, particularly less than 0.7 part by weight, based on 100 parts by weight of the initial amount of the poorly water-soluble drug.

In a preferable embodiment, it can be recognized that the quality standard is satisfied if the pharmaceutical composition contains, when stored at the accelerated condition (40° C.) for 6 months, a related substance of Formula 1a (particularly, Formula 1d) in an amount of less than 0.25 part by weight, particularly less than 0.22 part by weight, based on 100 parts by weight of the initial amount of the poorly water-soluble drug.

In a preferable embodiment, it can be recognized that the quality standard is satisfied if the pharmaceutical composition contains, when stored at the accelerated condition (40° C.) for 6 months, a related substance of Formula 1b (particularly, Formula 1e) in an amount of less than 0.55 part by weight, particularly less than 0.48 part by weight, based on 100 parts by weight of the initial amount of the poorly water-soluble drug.

It can be recognized that the quality standard is satisfied if the pharmaceutical composition of an embodiment of the present invention contains, when stored at the severe condition (80° C.) for 3 weeks, a related substance of Formula 1 (particularly, Formula 1c) in an amount of 1.0 part by weight or less, preferably 0.6 part by weight or less, more preferably 0.4 part by weight or less, even more preferably 0.2 part by weight or less, and most preferably 0.16 part by weight or less, based on 100 parts by weight of the initial amount of the poorly water-soluble drug.

In a preferable embodiment, it can be recognized that the quality standard is satisfied if the pharmaceutical composition contains, when stored at the severe condition (80° C.) for 3 weeks, a related substance of Formula 1a (particularly, Formula 1d) in an amount of 0.5 part by weight or less, preferably 0.3 part by weight or less, more preferably 0.2 part by weight or less, even more preferably 0.1 part by weight or less, and most preferably 0.08 part by weight or less, based on 100 parts by weight of the initial amount of the poorly water-soluble drug.

In a preferable embodiment, it can be recognized that the quality standard is satisfied if the pharmaceutical composition contains, when stored at the severe condition (80° C.) for 3 weeks, a related substance of Formula 1b (particularly, Formula 1e) in an amount of 0.5 part by weight or less, preferably 0.3 part by weight or less, more preferably 0.2 part by weight or less, even more preferably 0.1 part by weight or less, and most preferably 0.08 part by weight or less, based on 100 parts by weight of the initial amount of the poorly water-soluble drug.

In a preferable embodiment, it can be recognized that the quality standard is satisfied if the pharmaceutical composition of an embodiment of the present invention contains, when stored at the severe condition (80° C.) for 3 weeks, a related substance of Formula 1 (particularly, Formula 1c) in an amount of less than 0.45 part by weight, based on 100 parts by weight of the initial amount of the poorly water-soluble drug.

In a preferable embodiment, it can be recognized that the quality standard is satisfied if the pharmaceutical composition of an embodiment of the present invention contains, when stored at the severe condition (80° C.) for 3 weeks, a related substance of Formula 1a (particularly, Formula 1d) in an amount of less than 0.18 part by weight, based on 100 parts by weight of the initial amount of the poorly water-soluble drug.

In a preferable embodiment, it can be recognized that the quality standard is satisfied if the pharmaceutical composition of an embodiment of the present invention contains, when stored at the severe condition (80° C.) for 3 weeks, a related substance of Formula 1b (particularly, Formula 1e) in an amount of less than 0.27 part by weight, based on 100 parts by weight of the initial amount of the poorly water-soluble drug.

In the method for evaluating a polymeric micelle pharmaceutical composition of an embodiment of the present invention, it can be recognized that the quality standard is satisfied if the pharmaceutical composition contains, when stored at the accelerated condition (40° C.) for 6 months, a related substance of Formula 2 (particularly, Formula 2a) in an amount of 0.3 part by weight or less, preferably 0.25 part by weight or less, more preferably 0.2 part by weight or less, even more preferably 0.15 part by weight or less, and most preferably 0.1 part by weight or less, based on 100 parts by weight of the initial amount of the poorly water-soluble drug.

In a preferable embodiment, it can be recognized that the quality standard is satisfied if the pharmaceutical composition of an embodiment of the present invention contains, when stored at the accelerated condition (40° C.) for 6 months, a related substance of Formula 2 (particularly, Formula 2a) in an amount of less than 0.27 part by weight, particularly less than 0.19 part by weight, based on 100 parts by weight of the initial amount of the poorly water-soluble drug.

It can be recognized that the quality standard is satisfied if the pharmaceutical composition of an embodiment of the present invention contains, when stored at the severe condition (80° C.) for 3 weeks, a related substance of Formula 2 (particularly, Formula 2a) in an amount of 1.0 part by weight or less, preferably 0.8 part by weight or less, more preferably 0.6 part by weight or less, even more preferably 0.4 part by weight or less, and most preferably 0.2 part by weight or less, based on 100 parts by weight of the initial amount of the poorly water-soluble drug.

In a preferable embodiment, it can be recognized that the quality standard is satisfied if the pharmaceutical composition of an embodiment of the present invention contains, when stored at the severe condition (80° C.) for 3 weeks, a related substance of Formula 2 (particularly, Formula 2a) in an amount of less than 0.76 part by weight, based on 100 parts by weight of the initial amount of the poorly water-soluble drug.

The present invention is explained in more detail by the following examples. However, these examples seek to illustrate the present invention only, and the scope of the present invention is not limited by the examples in any manner.

EXAMPLES

Experimental Example 1-1: Isolation of Related Substances by Liquid Chromatography To a vial containing 100 mg of polymeric micelle composition containing paclitaxel, which had been subjected to the six-month acceleration test (temperature: 40° C.), 16.7 ml of deionized water (DW) was fed and the contents were completely dissolved, and the total amount of the liquid was taken and transferred to a 20-ml volumetric flask, and the marked line was met to make the total volume 20 ml (5.0 mg/ml). 2 ml of this liquid was taken and transferred to a 10-ml volumetric flask, and the marked line was met with acetonitrile to make the total volume 10 ml (1 mg/ml). For the above composition, related substance was isolated and fractionally collected using the following liquid chromatography.

Conditions for Liquid Chromatography
1) Column: Poroshell 120 pentafluorophenyl (PFP) (4.6× 150 mm, 2.7 μm, Agilent)
2) Mobile phase: A: DW/B: Acetonitrile

| Time (min) | % A | % B |
|---|---|---|
| 0.00 | 65 | 35 |
| 25.00 | 45 | 55 |
| 28.00 | 45 | 55 |
| 30.00 | 65 | 35 |
| 35.00 | 65 | 35 |

3) Flow rate: 0.6 ml/min
4) Injection volume: 10 μl
5) Detector: UV absorption spectrophotometer (Measurement wavelength: 227 nm)

The resulting chromatogram of HPLC analysis is shown in FIG. 1.

Experimental Example 1-2: Qualitative Analysis of Related Substances of RRT 1.10 and 1.12 Using LC/MS/MS The related substances isolated in Experimental Example 1-1 (RRT: 1.10±0.02 (1.08~1.12) and 1.12±0.02 (1.10~1.14)) were qualitatively analyzed by MS scan of liquid chromatography-mass spectrometer (LC/MS/MS). As the LC/MS/MS, liquid chromatography 1200 series and electrospray ionization mass spectrometer 6400 series (Agilent, US) were used. The conditions for analysis were as follows.

Conditions for Liquid Chromatography
1) Column: Cadenza HS-C18 (3.0×150 mm, 3 μm, Imtakt)
2) Mobile phase: A: 0.5 mM ammonium acetate with 0.03% acetic acid/B: Acetonitrile

| Time (min) | % A | % B |
|---|---|---|
| 0.00 | 80 | 20 |
| 4.00 | 55 | 45 |
| 9.00 | 55 | 45 |
| 9.10 | 80 | 20 |
| 15.00 | 80 | 20 |

3) Flow rate: 0.4 ml/min
4) Injection volume: 2 μl
5) Detector: UV absorption spectrophotometer (Measurement wavelength: 227 nm)

Conditions for Electrospray Ionization Mass Spectrometer
1) Ionization: Electrospray Ionization, Positive (ESI+)
2) MS Method: MS2 scan/Product ion scan
3) Ion source: Agilent Jet Stream ESI
4) Nebulizer gas (pressure): Nitrogen (35 psi)
5) Ion spray voltage: 3500 V
6) Drying gas temperature (flow rate): 350° C. (7 L/min)
7) Sheath gas temperature (flow rate): 400° C. (10 L/min)
8) Fragmentor: 135 V
9) Nozzle voltage: 500 V
10) Cell accelerator voltage: 7 V
11) EMV: 0 V
12) Collision energy: 22 V
13) Precursor ion: m/z 1020.2
14) Mass scan range: m/z 100~1500

The substance for analysis, which was isolated and came out of the detection stage, was set to flow in the mass spectrometer, and at that time the detected ion of related substance was qualitatively analyzed selecting the characteristic ion of mass spectrum [M+Na].

The resulting chromatogram and spectrum of LC/MS/MS analysis is shown in FIG. 2.

Experimental Example 2: Induction of Reaction of Paclitaxel and Lactide and HPLC Analysis of Reaction Product In the related substances which were fractionally collected from the polymeric micelle composition containing paclitaxel in Experimental Example 1-1, many polymers existed together and thus qualitative analysis thereof was very difficult. As a result of the qualitative analysis in the subsequently conducted Experimental Example 1-2, the related substances were presumed as compounds produced by combination of paclitaxel and lactide. Accordingly, an experiment of inducing a reaction by adding lactide to paclitaxel directly and analyzing the reaction product was carried out to confirm whether the presumed related substances were produced.

First, each of 5 mg of paclitaxel and 3 mg of L-lactide/D-lactide was dissolved in 1 ml of acetonitrile (ACN): DW=70:30 (v/v) solution, and the solutions were then mixed. This solution was transferred to an LC vial and analyzed by HPLC. The resulting chromatogram of HPLC analysis is shown in FIG. 3.

As a result of analysis, it could be confirmed that the compound of the combination of paclitaxel and L-lactide eluted first on the chromatogram and the compound of the combination of paclitaxel and D-lactide eluted later. Furthermore, in case of experiment using the same amount, it could be confirmed that the combination of paclitaxel and D-lactide was formed more than the combination of paclitaxel and L-lactide. Through this, the same pattern of chromatogram as that of the polymeric micelle composition containing paclitaxel, which had been subjected to the six-month acceleration test, could be confirmed.

Figure 4B:
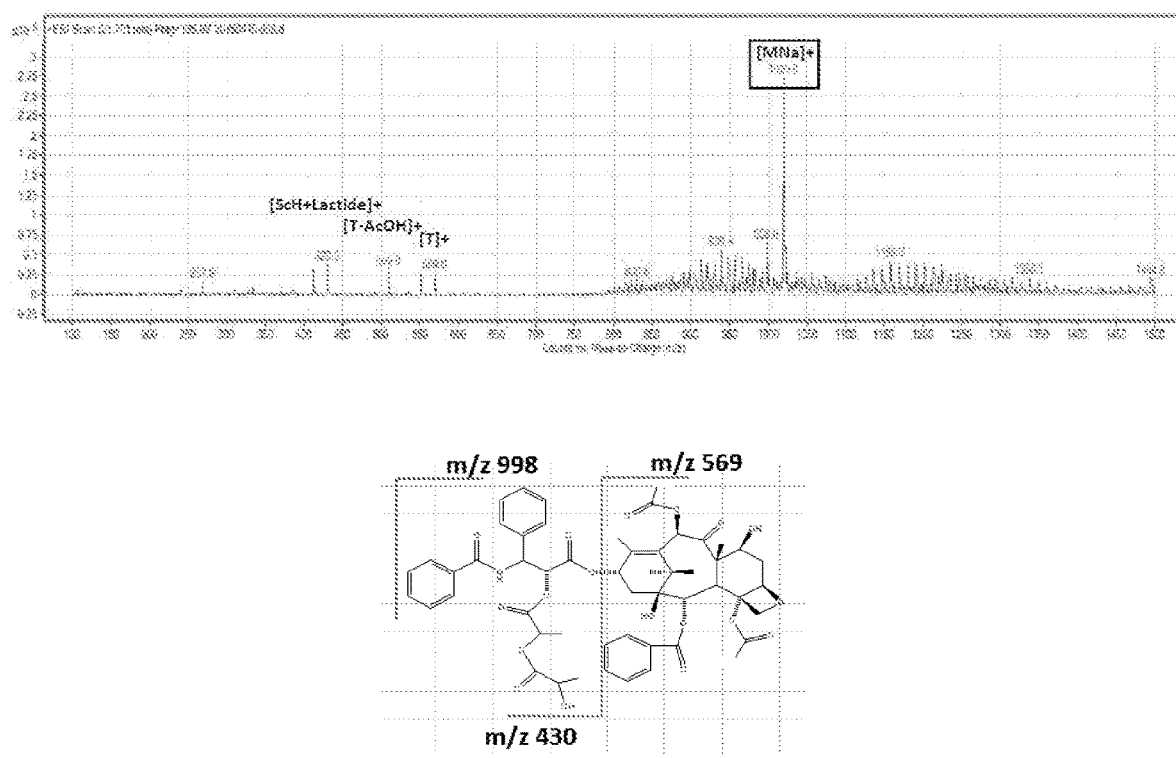
Figure 4C:
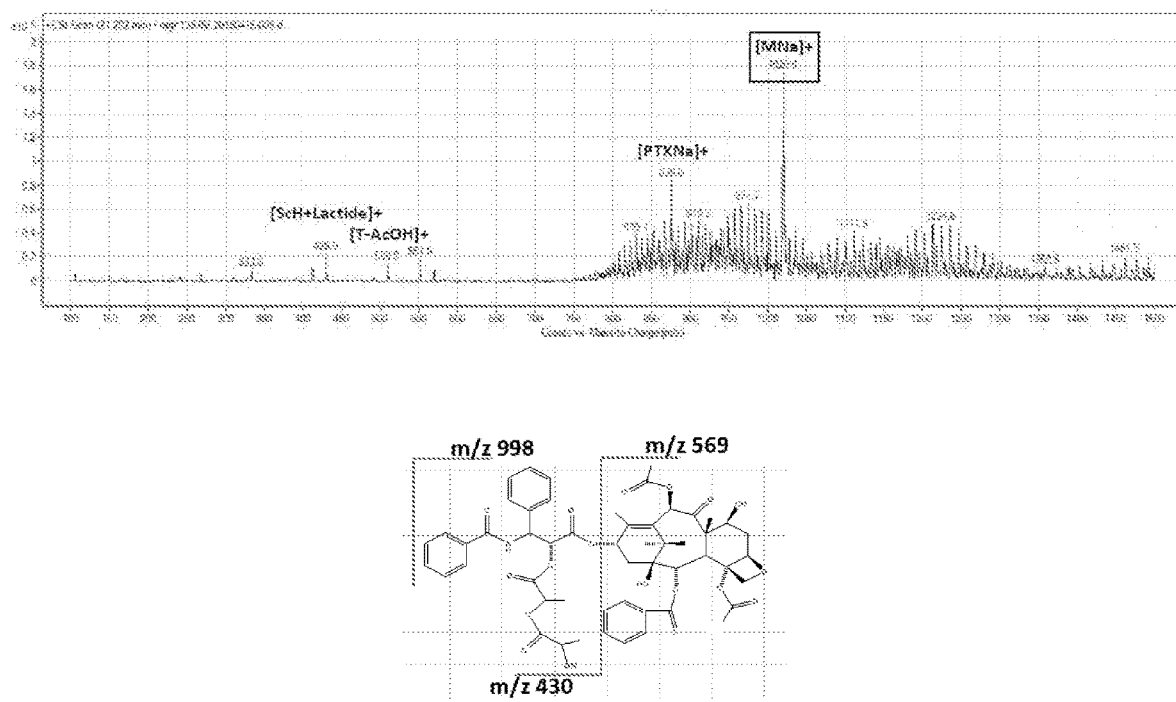

Experimental Example 3: Qualitative Analysis of Reaction Product of Paclitaxel and Lactide Using LC/MS/MS Using LC/MS/MS, a sample containing paclitaxel only was MS scanned first, and as a result thereof, m/z 854.2 amu which was [M+H]$^+$ and m/z 876.2 amu which was [M+Na]$^+$ appeared. After that, when L-lactide and D-lactide were added to paclitaxel, m/z 1020.0 amu, which was not shown in the sample containing paclitaxel only, appeared and it was confirmed that the intensity thereof continuously increased with the lapse of time. The resulting spectrum of LC/MS/MS analysis is shown in FIGS. 4A, 4B and 4C.

It could be confirmed again from this that the structure of the related substance obtained through Experimental Example 1-1 was the 1020.0 amu compound which was [M+Na]$^+$ produced by the combination of paclitaxel and lactide isomer.

From the results of Experimental Examples 2 and 3 and conventional knowledge of reaction in organic chemistry, it could be known that the related substance of the polymeric micelle composition was the following compound produced by the combination of paclitaxel and lactide.

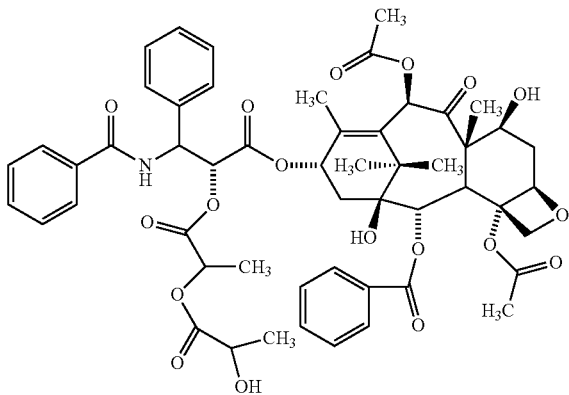

Combined form of paclitaxel and lactide: $C_{53}H_{59}NO_{18}$ (998.03 g/mol)

Experimental Example 4: Qualitative Analysis of Related Substance of RRT 0.87 Using LC/MS/MS The related substance isolated in Experimental Example 1-1 (RRT: 0.87±0.02 (0.85~0.89)) was qualitatively analyzed by MS scan and product ion scan of liquid chromatography-mass spectrometer (LC/MS/MS). In the following measurement, as the LC/MS/MS, liquid chromatography 1200 series and electrospray ionization mass spectrometer 6400 series (Agilent, US) were used. The conditions for analysis were as follows.

Conditions for Liquid Chromatography
1) Column: Poroshell 120 PFP (4.6×150 mm, 2.7 μm, Agilent)
2) Mobile phase: A: DW/B: Acetonitrile

| Time (min) | % A | % B |
|---|---|---|
| 0.00 | 65 | 35 |
| 25.00 | 45 | 55 |
| 28.00 | 45 | 55 |
| 30.00 | 65 | 35 |
| 35.00 | 65 | 35 |

3) Flow rate: 0.6 ml/min
4) Injection volume: 10 μl
5) Detector: UV absorption spectrophotometer (Measurement wavelength: 227 nm)

Conditions for Electrospray Ionization Mass Spectrometer
1) Ionization: Electrospray Ionization, Positive (ESI+)
2) MS Method: MS2 scan/Product ion scan
3) Ion source: Agilent Jet Stream ESI
4) Nebulizer gas (pressure): Nitrogen (35 psi)
5) Ion spray voltage: 3500 V
6) Drying gas temperature (flow rate): 350° C. (7 L/min)
7) Sheath gas temperature (flow rate): 400° C. (10 L/min)
8) Fragmentor: 135 V
9) Nozzle voltage: 500 V
10) Cell accelerator voltage: 7 V
11) EMV: 0 V
12) Collision energy: 22 V
13) Precursor ion: m/z 894.2
14) Mass scan range: m/z 100~1500

The substance for analysis, which was isolated and came out of the detection stage, was set to flow in the mass spectrometer, and at that time the detected ion of related substance was qualitatively analyzed selecting the characteristic ion of mass spectrum [M+Na].

Experimental Example 5: LC/MS/MS Analysis of Related Substance of RRT 0.87 in Mixture of Acid-Treated Paclitaxel As a result of the qualitative analysis of the polymeric micelle composition containing paclitaxel in Experimental Example 4, the related substance was presumed as a material produced when paclitaxel was treated with acid. To confirm this, a compound was prepared by adding 1N HCl to paclitaxel and analyzed by LC/MS/MS. The results of LC/MS/MS analysis are shown in FIG. 6, and the results of product ion scan in the LC/MS/MS analysis are shown in FIG. 7 together with the results of paclitaxel.

According to the analysis results, on the chromatogram, the material obtained at RRT 0.87 from the mixture obtained by treating paclitaxel with acid showed exactly the same HPLC peak as that of the related substance (RRT: 0.87±0.02 (0.85~0.89)) in the polymeric micelle composition containing paclitaxel of an embodiment of the present invention which had been subjected to the six-month acceleration test. In addition, since the two materials showed the same spectrum of product ion scan at RRT 0.87 (FIG. 7), it could be confirmed that the two materials have the same structure.

Experimental Example 6: NMR Analysis of Related Substance of RRT 0.87 Under the Same Analysis Method in Mixture of Acid-Treated Paclitaxel In order to verify the chemical structure of the related substance of RRT 0.87 under the same analysis method in mixture of acid-treated paclitaxel obtained by adding 1N HCl to paclitaxel, the same related substance was isolated and fractionally collected, and analyzed by NMR spectroscopy. In the NMR analysis, the results of $^1$H NMR analysis are shown in FIG. 8, the results of $^{13}$C NMR analysis are shown in FIG. 9, the results of COSY (Correlation Spectroscopy) analysis are shown in FIG. 10, and the results of HMBC (Heteronuclear Multiple Bond Correlation Spectroscopy) analysis are shown in FIG. 11.

According to the analysis results, it could be confirmed that the material shown at RRT 0.87 under the same analysis method by treating paclitaxel with acid (i.e., the related substance (RRT: 0.87±0.02 (0.85~0.89)) in the polymeric micelle composition containing paclitaxel of an embodiment of the present invention which had been subjected to the six-month acceleration test) was the compound of the following form of the combination of paclitaxel and water.

Combined form of paclitaxel and one molecule of water: $C_{47}H_{53}NO_{15}$ (871.94 g/mol)

Conditions for NMR (Nuclear Magnetic Resonance Spectroscopy)

1. $^1H$
   1) NMR equipment: Brucker DRX-300, AVANCE-400 equipped with a temperature controller
   2) Sample/Solvent: 1~10 mg sample/0.6 mL chloroform-d in 5 mm o.d. NMR tube (In all NMR experiments, the same sample was used.)
   3) Probehead: Brucker 5 mm QNP or C-H dual probe
   4) Proton 90° degree pulse width/Excitation angle/Acquisition time: 10.0~11.0 μsec/30°/~5.0 sec
   5) Relaxation delay/Number of scan: 1.0~5.0 sec/4~64

2. $^{13}C$
   1) Probehead: Brucker 5 mm QNP or C-H dual probe
   2) Carbon 90° degree pulse width/Excitation angle/Acquisition time: 10.0 μsec/30°/2.0~3.0 sec
   3) Relaxation delay/Number of scan: 2.0~5.0 sec/more than 5,000

3. COSY
   1) NMR equipment: Brucker AVANCE-400
   2) Probehead: Brucker 5 mm QNP
   3) Pulse sequence: cosygp pulse sequence
   4) Proton 90° degree pulse width/Acquisition time: 11.0 μsec/0.4~1.6 sec
   5) Relaxation delay/Number of scan/Number of experiments for ω1: 0.5~2.0 sec/32~48/400~500

4. HMBC
   1) NMR equipment: Brucker AVANCE-400
   2) Probehead: Brucker 5 mm inverse probe
   3) Pulse sequence: inv4gptp pulse sequence (for HMQC)/inv4gplprnd pulse sequence (for HMBC)
   4) Proton 90° degree pulse width/Carbon 90° degree pulse width/Acquisition time: 7.5 μsec/17~18 μsec/0.15~0.2 sec
   5) Relaxation delay/Number of scan for HMQC/Number of scan for HMBC/Number of experiments for ω1: 1.0~2.0 sec/32~96/224/128~256
   6) Temperature/1/2(JCH): 300K/3.5 msec.

The invention claimed is:

1. A method for evaluating a polymeric micelle pharmaceutical composition, comprising evaluating a polymeric micelle pharmaceutical composition, which comprises an amphiphilic block copolymer comprising a hydrophilic block (A) and a hydrophobic block (B), and paclitaxel or docetaxel as a poorly water-soluble drug, by using a compound represented by the following Formula 1 as a standard material;

wherein the hydrophilic block (A) comprises one or more selected from the group consisting of polyethylene glycol or derivatives thereof, polyvinylpyrrolidone, polyvinyl alcohol, polyacrylamide and combinations thereof; and the hydrophobic block (B) is polylactide:

Formula 1 wherein
$R_1$ is H or $C(O)CH_3$, and $R_2$ is phenyl or $OC(CH_3)_3$.

2. The method for evaluating a polymeric micelle pharmaceutical composition according to claim 1, wherein the poorly water-soluble drug is paclitaxel, the compound represented by Formula 1 is a compound represented by the following Formula 1c:

[Formula 1c]

3. The method for evaluating a polymeric micelle pharmaceutical composition according to claim 1, wherein the pharmaceutical composition is recognized as satisfying a quality standard if it contains, when stored at 40° C. for 6 months, the compound represented by Formula 1 in an amount of 0.8 part by weight or less, based on 100 parts by weight of an initial amount of the poorly water-soluble drug.

4. The method for evaluating a polymeric micelle pharmaceutical composition according to claim 1, wherein the compound of Formula 1 includes a compound of the following Formula 1a, a compound of the following Formula 1b, or both a compound of Formula 1a and a compound of Formula 1b:

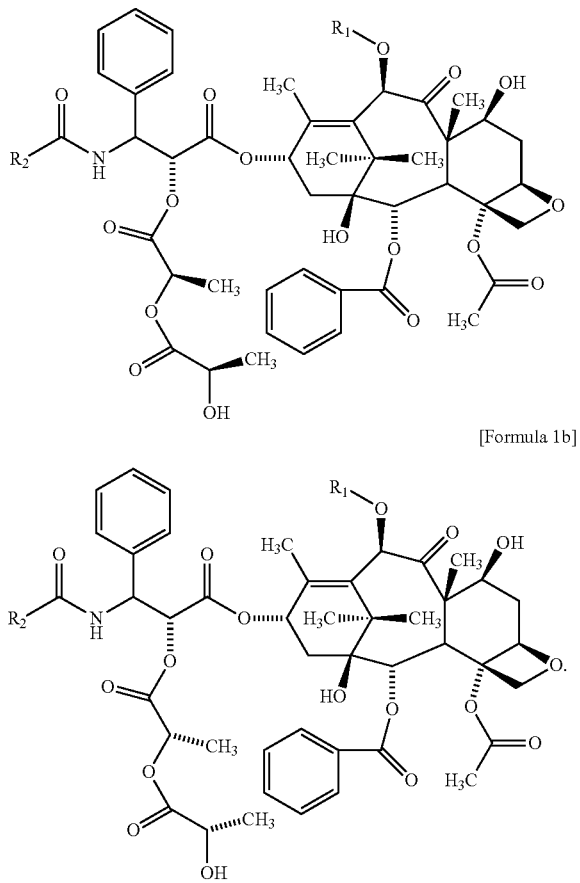

[Formula 1a]

[Formula 1b]

5. The method for evaluating a polymeric micelle pharmaceutical composition according to claim 4, wherein the pharmaceutical composition is recognized as satisfying a quality standard if it contains the compound of Formula 1a in an amount of 0.3 part by weight or less, based on 100 parts by weight of an initial amount of the poorly water-soluble drug, and the compound of Formula 1b in an amount of 0.5 part by weight or less, based on 100 parts by weight of an initial amount of the poorly water-soluble drug.

6. The method for evaluating a polymeric micelle pharmaceutical composition according to claim 1, wherein the polymeric micelle pharmaceutical composition is evaluated by analyzing the compound represented by Formula 1 by steps comprising:
(1) preparing a sample for analysis of the polymeric micelle pharmaceutical composition; and
(2) analyzing related substances in the prepared sample by high performance liquid chromatography (HPLC) using the following conditions (a) and (b):
(a) a stationary phase of porous particles having a particle size of 4 μm or less; and
(b) a column having an inner diameter of 5 mm or less and a length of 50 mm or more.

7. The method for evaluating a polymeric micelle pharmaceutical composition according to claim 6, wherein the stationary phase of porous particles is a pentafluorophenyl stationary phase.

8. The method for evaluating a polymeric micelle pharmaceutical composition according to claim 6, wherein the high performance liquid chromatography is carried out by using a stationary phase of porous particles having a particle size of 1.5 to 4 μm and a column having an inner diameter of 2 to 5 mm and a length of 50 to 250 mm.

9. The method for evaluating a polymeric micelle pharmaceutical composition according to claim 6, further comprising qualitatively analyzing the related substances, which are isolated in step (2) by liquid chromatography/mass spectrometry (LC/MS), liquid chromatography/mass spectrometry/mass spectrometry (LC/MS/MS), nuclear magnetic resonance (NMR) or a combination thereof.

10. The method for evaluating a polymeric micelle pharmaceutical composition according to claim 9, wherein the LC/MS or LC/MS/MS is carried out by using (c) a hybrid octadecyl-silica (ODS) stationary phase; and (d) a column having an inner diameter of 10 mm or less and a length of 500 mm or less.

11. The method for evaluating a polymeric micelle pharmaceutical composition according to claim 6, wherein an ultraviolet (UV) detector is used to detect the related substances.

12. The method for evaluating a polymeric micelle pharmaceutical composition according to claim 6, wherein the hydrophilic block (A) is polyethylene glycol or monomethoxypolyethylene glycol.

13. The method for evaluating a polymeric micelle pharmaceutical composition according to claim 6, wherein the hydrophilic block (A) has a number average molecular weight of 200 to 20,000 Daltons; and the hydrophobic block (B) has a number average molecular weight of 200 to 20,000 Daltons.

* * * * *